United States Patent [19]
Isono et al.

[11] Patent Number: 5,114,004
[45] Date of Patent: May 19, 1992

[54] FILLED AND SEALED, SELF-CONTAINED MIXING CONTAINER

[75] Inventors: Keinosuke Isono, Kawaguchi; Takao Yoshida, Tama; Tatsuo Suzuki, Machida, all of Japan

[73] Assignee: Material Engineering Technology Laboratory Inc., Tokyo, Japan

[21] Appl. No.: 654,037

[22] Filed: Feb. 12, 1991

[30] Foreign Application Priority Data

Feb. 14, 1990 [JP] Japan .................................. 2-33515
Feb. 27, 1990 [JP] Japan .................................. 2-48286

[51] Int. Cl.⁵ .................... B65D 25/08; B67D 5/00; A61B 19/00
[52] U.S. Cl. .................................. 206/222; 222/80; 222/94; 222/145; 604/410; 604/416
[58] Field of Search .............. 206/219, 221, 222; 604/410, 416; 222/80, 129, 145, 94

[56] References Cited

U.S. PATENT DOCUMENTS

| | | | |
|---|---|---|---|
| 2,663,298 | 12/1953 | Rose | 206/221 X |
| 2,756,874 | 7/1956 | Erickson et al. | 206/221 |
| 3,110,308 | 11/1963 | Bellamy, Jr. | 604/410 X |
| 3,404,811 | 10/1968 | Cernei | 206/222 X |
| 3,542,032 | 11/1970 | Spencer, Jr. | 206/221 X |
| 3,608,709 | 9/1971 | Pike | 206/219 |
| 3,692,493 | 9/1972 | Terasaki | 604/416 X |
| 4,458,733 | 7/1984 | Lyons | 206/219 X |
| 4,484,920 | 11/1984 | Kaufman et al. | 604/416 |
| 4,884,703 | 12/1989 | O'Meera | 222/94 X |

FOREIGN PATENT DOCUMENTS

| | | |
|---|---|---|
| 2578530 | 9/1986 | France . |
| 83/01569 | 5/1983 | PCT Int'l Appl. . |
| 2134067 | 8/1984 | United Kingdom . |

Primary Examiner—Bryon P. Gehman
Attorney, Agent, or Firm—Cushman, Darby & Cushman

[57] ABSTRACT

Disclosed herein is a filled and sealed, self-contained mixing container. The container has compartments which are isolated from each other. Plural substances which contain components susceptible to mutual reaction unless isolated from each other are contained in the respective compartments. In use, these compartments are communicated together so that the individual contents can be mixed within the container. A flow passage or passages, each of which has an isolator for the contents and is adapted to communicate the compartments with each other, and is formed by a side channel provided on an outer surface of a wall of the container. Mixing of the contents without exposure to the external atmosphere can be realized by irreversible destruction of the isolator upon use. The container is suited particularly for a closed therapy system.

13 Claims, 9 Drawing Sheets

FIG.15
FIG.16
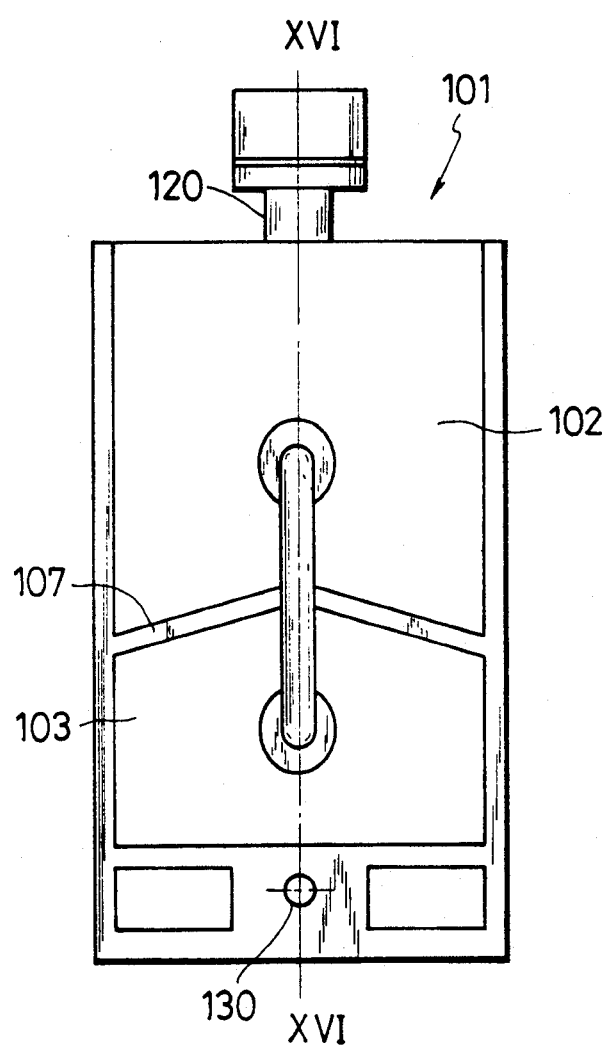
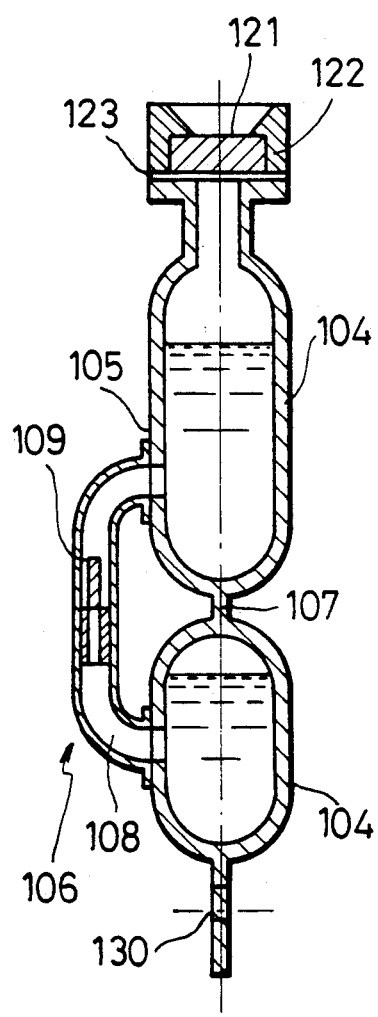

FILLED AND SEALED, SELF-CONTAINED MIXING CONTAINER

BACKGROUND OF THE INVENTION

1. Field of the Invention

This invention relates to a filled container with plural contents sealed within compartments in a manner isolated from each other, and more specifically to a filled and sealed, self-contained mixing container with plural contents, which contain components susceptible to mutual reaction, sealed therein in a mutually-isolated manner in advance, said container permitting simple and easy mixing of the plural contents without exposure to the external atmosphere upon use.

The container is suited particularly as a deformable container filled with plural drug preparations containing components susceptible to mutual reaction, such as medical fluids for intravenous hyperalimentation (IVH) or components for elemental diet (hereinafter abbreviated "ED"), said solutions or components being useful in a closed therapy system.

2. Description of the Related Art

There is a longstanding demand for containers which permit mixing of two types of drugs or the like in a self-contained manner immediately before use. This demand is especially strong, e.g., for heating or cooling media making us of reaction heat available upon mixing of two substances or for foods or drugs many of which tend to vary in nature if their ingredients or components are fed as a mixture to the production lines or are stored as a mixture over a long time.

Among these, drugs are each composed of plural chemical substances. Many of such drugs therefore tend to undergo variations with the passage of time if such chemical substances are subjected as a mixture to a heat-treatment step or are stored as a mixture over a long time.

For example, medical fluids for intravenous hyperalimentation which has been increasingly practiced in recent years are, from the above-described viewpoint, one example of drug preparations which generally are unsuited to formulation into single-pack preparations.

Intravenous hyperalimentation is applied where oral administration is insufficient or impossible as in the case of a ruptured suture in digestive tracts or problems of passage through digestive tracts, where oral administration is not preferred as in the case of inflammatory intestinal diseases or severe diarrhea, where high-calory replenishment exceeding replenishment per intestine is desired as in the case of extensive burns or severe multiple wounds, or where it is desired to treat a metabolic disorder caused by a disease such as hepatic insufficiency, renal insufficiency or glycogen storage disease.

It is therefore essential that a medical fluid for intravenous hyperalimentation contains all nutrients, which are required for the body, in appropriate amounts. The medical fluid is therefore a multi-component medical fluid containing glucides, amino acids, lipids, primary electrolytes, trace elements and vitamins. In view of their compatibility, their stability in production steps and the stability of the resultant medical fluid over a prolonged period of time, it is impossible under the circumstances to formulate them into a single composite solution. For example, if glucose and amino acids are combined together and filled as a single-pack liquid preparation in a container, reactions may take place between the glucose and the amino acids during autoclave sterilization treatment or during storage so that the medical fluid may be colored or may vary in quality.

Accordingly, the following three methods are now employed:

(1) A commercially-available base solution for intravenous hyperalimentation is used, which is a solution obtained by adding primary electrolytes to a high-concentration glucose solution. Before use, amino acids are added, followed by the addition of vitamins and any electrolytes for which reinforcement is required.

(2) A hypertonic glucose solution and an amino acid solution, which are both available on the market, are administered after mixing them together or by connecting them together.

(3) A base solution for intravenous hyperalimentation or a glucose solution is prepared by a hospital or clinic itself in its manufacturing laboratory.

Whichever method is used, it is the current situation that an amino acid solution is mixed in a base solution for intravenous hyperalimentation or a hypertonic glucose solution at the time of use and the resultant mixture is then administered to a patient.

A drug preparation which tends to lose stability when stored in the form of a solution, like ED, and cannot therefore be stored over a prolonged period of time is stored by dividing it into a powder drug portion and a liquid drug portion. These two portions are combined together immediately before use, followed by administration to a patient.

The method in which two or more components are mixed together at the time of use as described above needs a complex operation with the result that it has the potential danger of induction of preparation errors. In addition, the mixing cannot be performed in any complete closed system so that from the standpoint of safety for the hospital infection the above method also lacks adequate protection. There is accordingly a strong demand for a container which permits mixing by a simple operation in a complete closed system immediately before use.

Further, with the ever-increasing interest in home health care in recent years, there is also a desire for the development of a system which permits fail-free sure mixing of plural medicinal components so that transfusion or the like can be easily practiced at home in the future.

Filled and sealed, self-contained mixing containers have recently been put on the market, in each of which plural compartments are connected together, the points of connection are provided with isolation means capable of communicating the plural compartments to each other, and the isolation means is manipulated immediately before use to communicate the plural compartments to each other so that plural drug components filled in the plural compartments can be mixed in one of the compartments.

Conventionally known isolation means include plugs and clips. In the case of a plug, it is provided fixedly at an isolating portion dividing a single container into plural compartments. At the time of use, the plug is broken from the outside of the container to communicate the plural compartments to each other. When a clip is employed, an isolating portion dividing a single container into plural compartments is partly opened and this open portion is externally closed by the clip. The former plug method however requires arrangement of a plug, which has been fabricated separately, in a container and subsequent bonding of the plug to the container. There is hence a high potential danger that the interior of the container may be contaminated at this time. Moreover, this bonding of the plug to the container is rather difficult and a limitation may be imposed on the material. For example, to bond a three-dimensional structure such as the plug method described above, high-frequency welding is suited but heat sealing is not. Materials which can be bonded by high-frequency welding are however limited to those having a large dielectric loss such as polyvinyl chloride resin, ethylene-vinyl acetate copolymers and soft polyester resins. It has hence been difficult to use polyolefin resins for their small dielectric loss despite their high safety for the body and their low material cost.

On the other hand, the latter clip method does not permit confirmation of opening of an isolating portion even when the isolating portion is opened during transportation or storage unless such opening takes place at a time permitting its observation, for example, in use. Namely, the clip method is totally unguarded against mischief or the like. A very serious problem is therefore involved in the construction of a pharmaceutical system, for which securement of safety is a keynote, by the clip method.

SUMMARY OF THE INVENTION

An object of the present invention is to provide a filled and sealed, self-containing mixing container which permits sterilization treatment of plural contents, said contents containing components susceptible to mutual reaction, storage over a prolonged period of time while maintaining them in a stable state, and simple and easy mixing of the contents at the time of use.

In one aspect of the present invention, there is thus provided a flexible, plastic, filled and sealed, self-contained mixing container consisting of plural compartments with contents enclosed therein in a manner mutually isolated from each other. The container comprises:
- a side channel or side channels formed on a two-dimensionally developable outer surface of a wall of the container, said side channel or side channels extending over the plural compartments; and
- a contents isolator provided inside the side channel, said isolator being irreversibly destructible in order to mix the contents together.

As the side channel, there are several embodiments. In a first embodiment, the side channel has a bubble-like shape, the isolator is formed of the wall of the container itself, and a means for destroying the isolator is provided inside the side channel. In a second embodiment, the side channel is in the form of a tube, and the isolator is formed as a self-destructible member discrete from the tube and is provided inside the tube. Two types of isolators can be used, one requiring another member upon destruction and the other requiring no separate member.

According to the filled and sealed container of the present invention, plural contents containing components susceptible to mutual reaction are retained in a mutually-isolated state in plural compartments, respectively. It is hence possible to store the plural contents without modifications for a prolonged period of time until immediately before use even when the contents are subjected to sterilization in an autoclave. Moreover, at the time of use, the plural contents can be mixed easily without their exposure to the external atmosphere by manipulating the isolator to communicate the plural compartments to each other.

The sealing by the isolator is extremely good owing to the structure of the isolator. Since the isolator is irreversibly destroyed, mixing of the contents can be easily discovered should the isolator be broken. The isolator is therefore very effective for maintaining the quality. Further, production steps of the container can all be performed by working, processing and/or machining from the outside. It is hence possible to produce the container while maintaining a high standard of cleanliness of the inside of the container. The present invention can provide therefore an economical, filled and sealed container with good productivity.

In particular, use of the filled and sealed container of this invention as a medical fluid container can bring about the following additional merits.

A filled and sealed container having high safety can be produced because the container can be made using polyolefin resins alone. One or more flexible resins can be chosen for the container, thereby making it possible to assemble an ideal, closed transfusion system.

BRIEF DESCRIPTION OF THE DRAWINGS

FIG. 15 a schematic front view showing a container according to a second embodiment of the present invention, said container having plural compartments filled with drug components and being equipped with a first example of tube-type side channel;

FIG. 16 is a cross-sectional view of the container of FIG. 15, taken along line XVI—XVI;

DETAILED DESCRIPTION AND THE PREFERRED EMBODIMENTS

This invention provides a container which permits fail-free isolation of plural contents until use and their easy mixing in a sealed state at the time of use, in other words, a self-contained mixing container. A structural feature of the container resides in the provision of the side channel. Owing to this structure, the production steps have been simplified substantially, the cleanliness inside the container has been markedly improved, and the sealing is sure.

The side channel is provided internally with a contents isolator which can be irreversibly destroyed upon mixing the contents. The side channel is self-opening so that the above-described destruction can be easily achieved without impairing the fluid tight property of the side channel. Preferred examples of such a side channel include bubble-type or blister-type and tube-type.

A description will hereinafter be made of modifications of such examples. Firstly, in the case of a bubble-type or blister-type side channel, an isolator is formed of a wall which in turn forms at least one of plural compartments. The side channel is therefore similar to a bubble formed at a boundary of the compartments. This side channel is excellent from the standpoints of both production and fluid tightness, because the isolator is formed using the compartment wall itself without employing any additional member.

Figure 1:
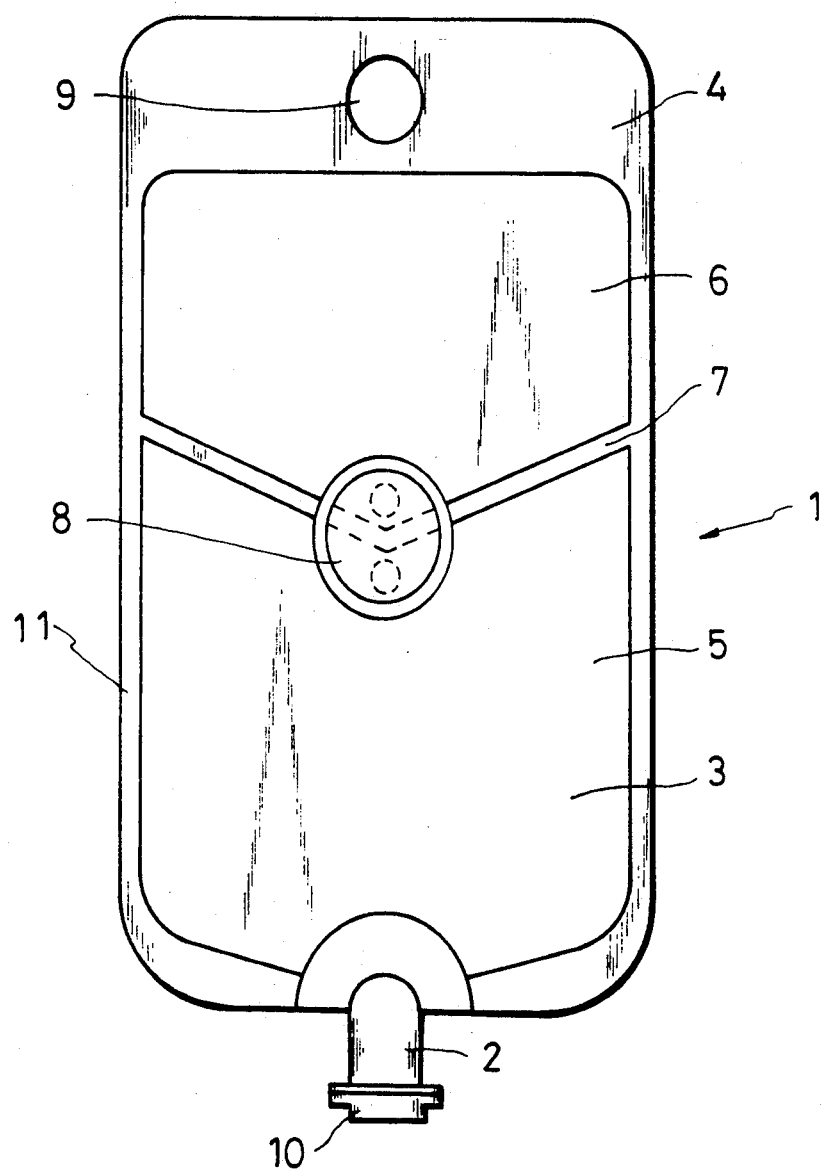
FIG. 1 is a schematic front view of a container having plural compartments filled with drug components according to a first embodiment of the present invention.

A filled and sealed container 1 according to a first embodiment, said container 1 having plural compartments, is depicted in FIG. 1. In the filled and sealed container 1, a first compartment 5 and a second compartment 6 which have been formed by sealing a pair of flexible sheets, said sheets being superimposed in a face-to-face relation, along peripheral edges thereof are integrally connected to each other with an isolation zone 7 interposed therebetween. A side channel 8 is bonded fluid tight on an outer surface of the container portion 3 in such a way that the side channel 8 extends across the isolation zone 7. In view of the bonded structure of the side channel 8, the outer surface of the container portion is required to be spreadable two-dimensionally.

The illustrated container 1 includes the two compartments. It is however to be noted that the number of compartments is determined in accordance with the kinds of contents to be used and ca therefore be determined as desired, because the container of the present invention can function irrespective of the number of compartments.

Contents to be stored inside the compartments will be described subsequently. In this invention, they are not limited to drugs for therapeutic applications, but contents susceptible to mutual reaction can be suitably stored. In particular, the application of the present invention to medical fluid bags for therapeutic use makes it possible not only to prevent quality modifications or deteriorations of the contents due to variations during autoclave sterilization treatment or with the passage of time but also to effectively avoid contamination by bacteria upon mixing medical fluids in a hospital. Further, it is also possible to easily improve the level of cleanliness inside the bags, namely, the containers by choosing a suitable production process. The advantageous effects of the present invention are therefore expected to be brought about most markedly in the above application field.

To use the container of this invention for storing medical fluids, it is desirable, as structural features to be used upon administration of the medical fluids to the body, to provide the container with an outlet member 2 having a plug 10 fitted therein, namely, a port for permitting discharge of the medical fluids from the container—at one end of the container—and with a suspension portion 4, namely, a portion defining a suspension hole 9 adapted to hang up the container on a irrigator stand—at the other end of the container.

The present invention is not limited to the use of only one outlet member. Each compartment may be provided with its own outlet member. The present invention permits provision of outlet members as many as desired and also allows to choose the dimensions and location of each outlet member as needed, both in view of convenience in use. This also applies similarly to the suspending portion.

Figure 2:
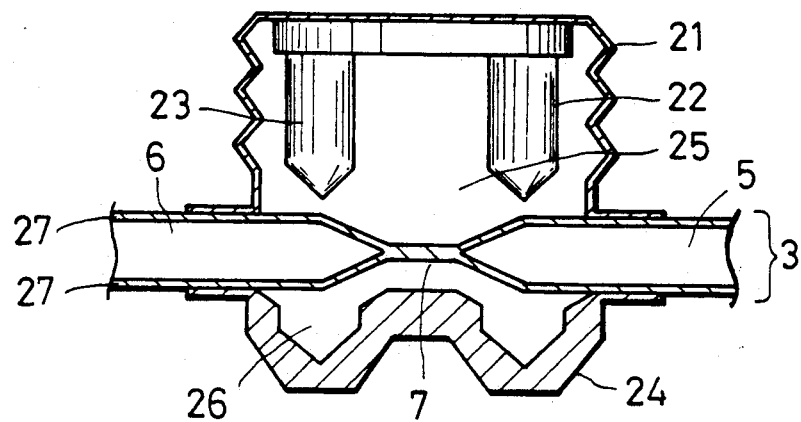
FIG. 2 is a schematic cross-sectional view showing a first example of a bubble-type side channel.

The side channel 8 can take various shapes. A specific shape according to a first example of the side channel is illustrated in FIG. 2. The side channel 8 is constructed of a communication enclosure 21, puncture members 22,23 as a destroying means, and a base 24. The communication enclosure 21 has an expandable and contractible, bellows-like shape to facilitate the understanding of its operation and function. The communication enclosure 21 is bonded fluid tight on an outer surface of one of walls, i.e., plastic sheets 27,27 of the container portion 3, whereby a communication compartment 25 is formed. The puncture members 22,23 are secured on an inner surface of a top wall of the communication enclosure 21. The base 24 is bonded fluid tight on an outer surface of the other one of the plastic sheets 27,27 of the container portion 3 at a position opposing the communication enclosure 21, so that another communication compartment 26 is formed. This communication compartment 26 also serves as a second side channel. It is to be noted that this communication compartment 26 is not essential, since the communication compartment 25 has already been formed as a communication channel for the first compartment 5 and the second compartment 6.

Figure 12:
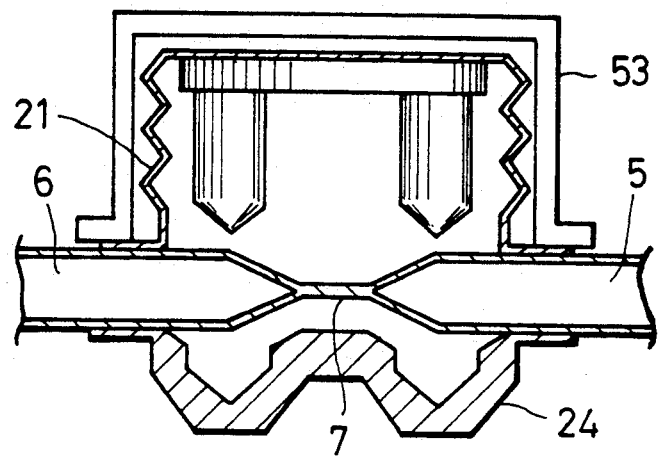
FIG. 12 is a schematic cross-sectional view showing a stopper arranged over the side channel.

Further, to avoid any accidental penetration of the puncture members 22,23 through the plastic sheets 27,27 during storage or transportation of the container, a means such as a stopper 53 shown in FIG. 12 may also be provided so that the bellows-like side walls of the communication enclosure 21 are prevented from expansion and contraction.

Operation of the container 1 will next be described. The communication enclosure 21 is pressed down by fingers or the like so that the puncture members 22,23 are caused to penetrate through the plastic sheets 27,27 which in combination form the first compartment 5 and the second compartment 6. This state is depicted in FIG. 3.

Figure 3:
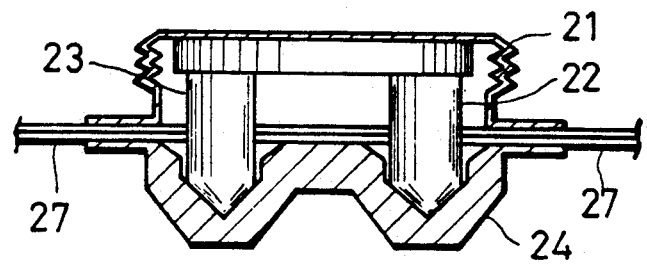
FIG. 3 is a schematic cross-sectional view in which through-holes are being formed by puncture members.

Although the puncture members 22,23 are caused to penetrate both the plastic sheets 27,27 in FIG. 3, the puncture members 22,23 may be used to puncture only one of the plastic sheets, namely, the upper plastic sheet 27. In this case, the base 24 is not required so that the side channel may be constructed without the base 24. Namely, the communication enclosure 21 can serve as a side channel provided that only one of the opposing plastic sheets 27,27 is punctured by the puncture members 22,23. To facilitate this, it is convenient to keep the plastic sheets 27,27 separated at a certain interval during the puncture although they are in full contact in FIG. 3. When the base is omitted, it is desirable to enhance the strength of the lower plastic sheet 27 at a position corresponding to the puncture members 22,23. This can be achieved by bonding a further sheet of the same kind and quality to the lower plastic sheet 27 to give a greater thickness at the position where the puncture members 22,23 may contact the lower sheet 27. As an alternative, a thicker plastic sheet may be used as the lower plastic sheet 27.

It is preferable to attach an air-pervious but water-impervious filter to a portion of the communication enclosure 21 where the communication compartment 25 is in a completely sealed state, pressing of the communication enclosure 21 results in compression of air inside the communication compartment 25 and large force is hence required to cause penetration of the puncture members 22,23 through the plastic sheets 27,27. Such a filter permits passage air without leakage of an aqueous solution therethrough so that the puncture members 22,23 can be easily caused to penetrate through the plastic sheets 27,27 without increasing the internal pressure of the communication compartment 25.

No adverse effects are given to the quality of the contents until use even if the communication enclosure 21 is made of an air-permeable material, because the individual compartments are isolated from each other by their own walls.

Figure 4:
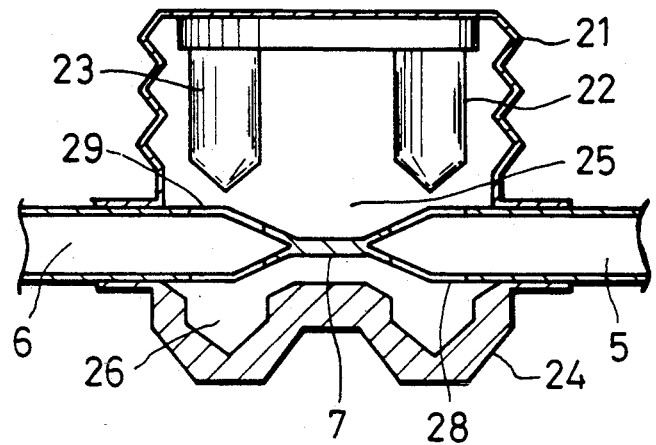
FIG. 4 is a schematic cross-sectional view of the plural compartments communicated together by way of the side channel in which the through-holes have been formed.

Next, the communication enclosure 21 is allowed to assume the original position. This state is shown in FIG. 4. Through-holes 28,29 have been formed for the first compartment 5 and the second compartment 6, respectively, whereby the first compartment 5 and the second compartment 6 are communicated with each other. The respective contents which have been sealed in the first and second compartments 5,6, respectively, can not be mixed together inside the container portion 3.

The communication enclosure 21 for the formation of the side channel 8 according to the first example shown in FIG. 2 had the expansible and contractible, bellows-like structure. The communication enclosure 21 can however take any shape insofar as it is expansible and contractible while retaining the sealed state. Further, an elastic, rubberlike material can be used as the material for the communication enclosure. The structure of the communication enclosure is therefore not necessarily limited to the bellows-like shape.

Figure 13:
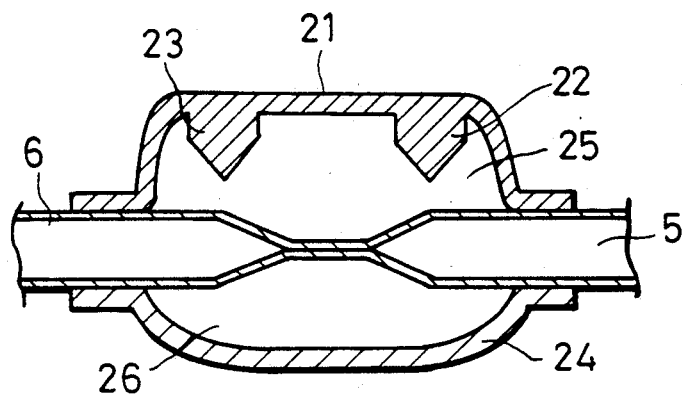
FIG. 13 is a schematic cross-sectional view showing a fourth example of the bubble-type side channel.

For the sake of simplicity, the communication enclosure can be an integral, molded, plastic article having a thickness of an order such that the article has sufficient shape retention. The plastic article internally has one or more puncture members and can be pressed with fingers at a top surface thereof. Such a article is illustrated in FIG. 13.

Figure 5:
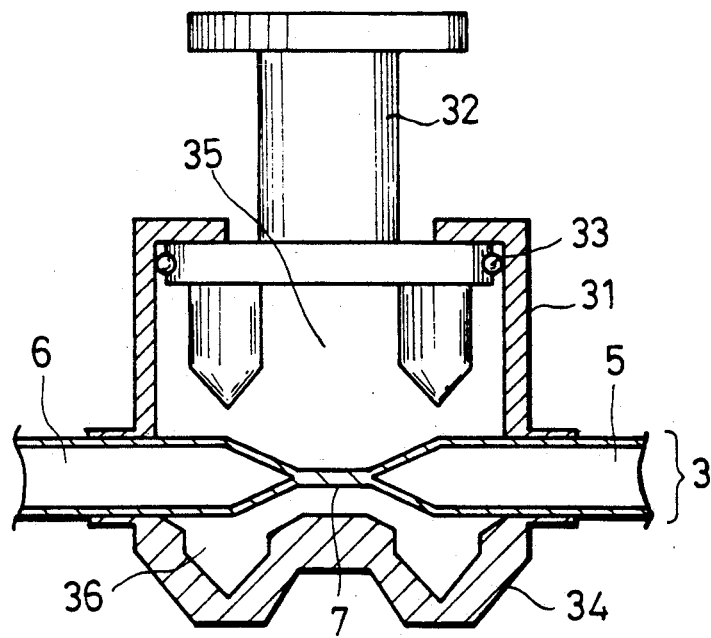
FIG. 5 is a schematic cross-sectional view showing a second example of the bubble-type side channel.

A second example of the side channel 8 is depicted in FIG. 5. The side channel 8 is constructed of a communication enclosure 31, a puncture member 32, an O-ring 33 and a base 34. The communication enclosure 31 and the puncture member 32 are assembled using the O-ring 33, so that the puncture member 32 is slidable fluid tight. The communication enclosure 31 is bonded fluid tight on an outer surface of one of plastic sheets 37,37 which in combination form the container portion 3, whereby a communication compartment 35 is defined. The base 34 is bonded fluid tight on an outer surface of the other plastic sheet 37 of the container portion 3 at a position opposing the communication enclosure 31, whereby another communication compartment 36 is formed.

Figure 6:
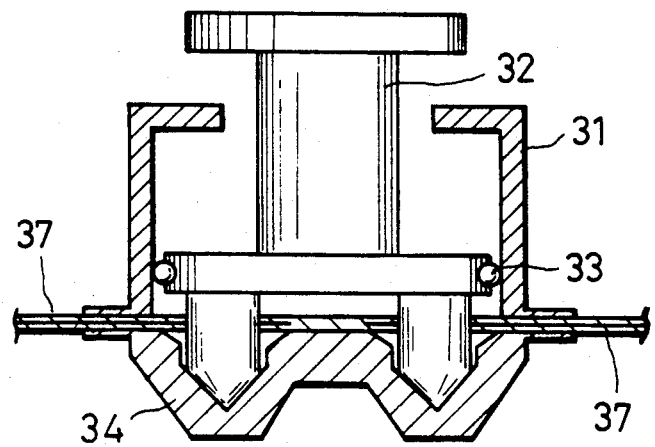
FIG. 6 is a schematic cross-sectional view in which through-holes are being formed by a puncture member.

The puncture member 32 is pressed to make the puncture member 32 penetrate through the plastic sheets 37,37 which in combination define the first and second compartments 5,6. This state is illustrated in FIG. 6.

Figure 7:
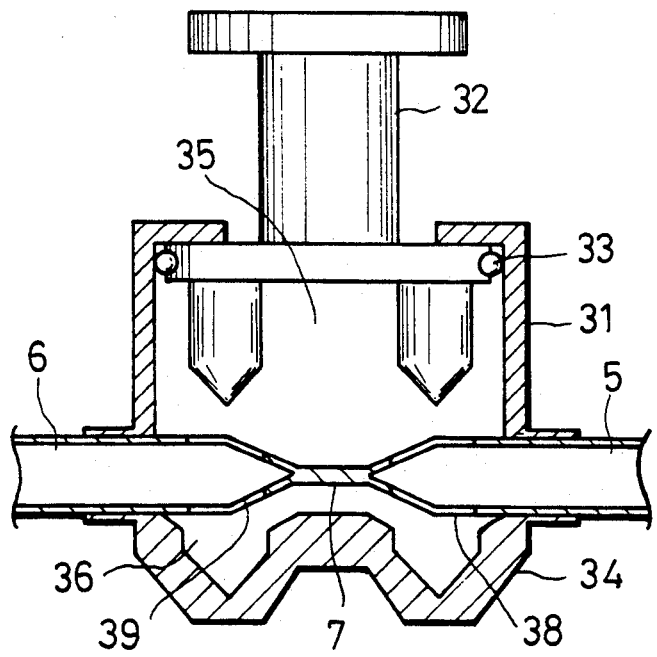
FIG. 7 is a schematic cross-sectional view of the plural compartments communicated together by way of the side channel in which the through-holes have been formed.

Next, the puncture member 32 is allowed to assume its original position. This state is shown in FIG. 7. The first and second compartments 5,6 have now been provided with through-holes 38,39, respectively. The first compartment 5 and the second compartment 6 are therefore communicated via communication compartments 35,36, so that the individual contents sealed within the first and second compartments 5,6, respectively can now be mixed inside the container portion 3.

Figure 8:
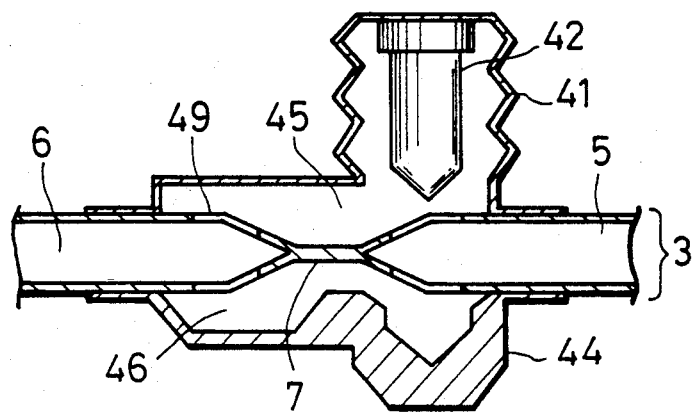
FIG. 8 is a schematic cross-sectional view showing a third example of the bubble-type side channel.

A third example of the side channel 8 is shown in FIG. 8. In this drawing, an isolator dividing the first and second compartments 5,6 from each other is the wall 7 on a side of the first compartment 5. On a side of the second compartment 6, a through-hole (communication hole 49) has already been formed. A communication means is constructed of a communication enclosure 41, a puncture member 42 and a base 44. The communication enclosure 41 has an expansible and contractible, bellows-like shape. The communication enclosure 41 is bonded fluid tight on an outer surface of one of plastic sheets 47,47 of the container portion 3, whereby a communication compartment 45 is formed. The puncture member 42 is fixed on an inner surface of a top wall of the communication enclosure 41. The base 44 is bonded fluid tight on an outer surface of the other plastic sheet 47 at a position opposing the communication enclosure 41, so that another communication compartment 46 is formed. The communication hole 49 has been formed beforehand at parts of the plastic sheets which define the second compartment 6. The communication hole 49 may be formed through both the plastic sheets 47,47 or through either one of the plastic sheets 47,47.

Figure 9:
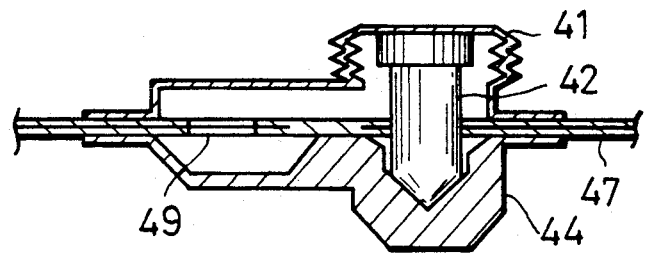
FIG. 9 is a schematic cross-sectional view in which through-holes are being formed by a puncture member.

The communication enclosure 41 is pressed to make the puncture member 42 penetrate the plastic sheets 47,47 which in combination define the first compartment 5. This state is depicted in FIG. 9.

Figure 10:
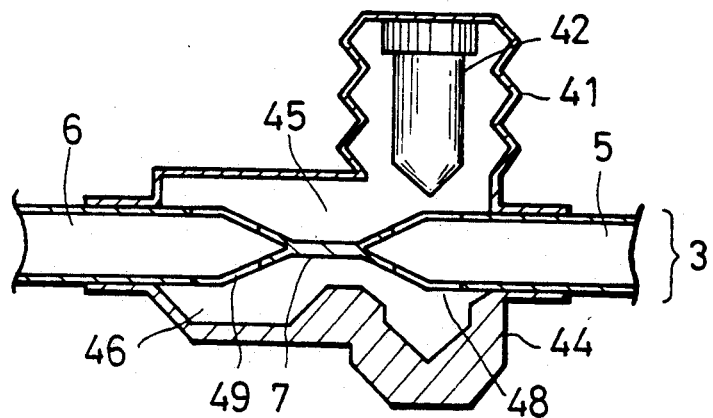
FIG. 10 is a schematic cross-sectional view of the plural compartments communicated together by way of the side channel in which the through-holes have been formed.

The communication enclosure 41 is then allowed to assume the original position. This state is shown in FIG. 10. A through-hole 48 has been formed in communication with the first compartment 5, whereby the first compartment 5 and the second compartment 6 are communicated via communication compartments 45,46 and the individual contents sealed within the first and second compartments 5,6, respectively can now be mixed inside the container portion 3. The mixing after the communication can be practiced by a simple operation, for example, by pressing the container with a hand since the container itself is flexible.

Figure 14:
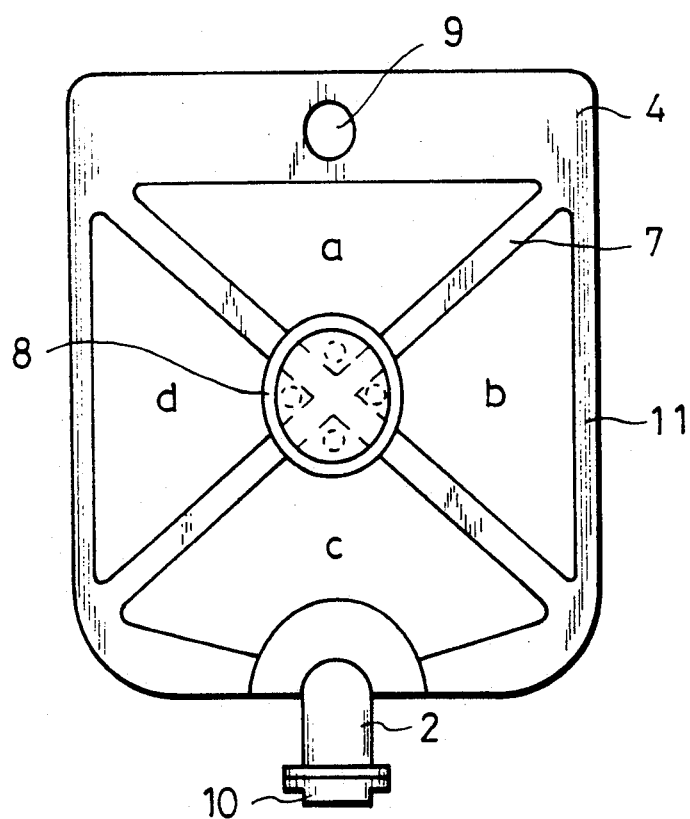
FIG. 14 is a schematic cross-sectional view of a container according to one modification of the first embodiment of the present invention, said container having four compartments filled with drug components and being provided with a bubble-type side channel.

In the above-described embodiment, the container was equipped with the two compartments. In the case of a container having, for example, four compartments, it can also be constructed likewise. A single side channel may be provided at a position such that the side channel extends over all the compartments. As an alternative, two side channels may be provided, one capable of connecting two of the compartments and the other the remaining two compartments. These two side channels can then be communicated together so that all the four compartments can be communicated together eventually. FIG. 14 shows one modification of the filled and sealed, self-contained mixing container according to the first embodiment of the present invention, in which modification the container defines four compartments a,b,c,d and has only one side channel. All the four compartments a,b,c,d can be communicated together by the single side channel. This structure is therefore very simple and requires only one communicating operation.

In the above-described embodiment of the present invention, the isolator or isolators for the respective contents are formed using the compartment-defining walls without the need for any additional material. This makes it possible to perform the production of each container itself independently from its corresponding side channel. Moreover, a very simple method can be chosen for the bonding between the container and the side channel. As a result, the production process and facilities can be simplified, leading to an economical production cost. In addition, the container can be produced under such conditions that the inside of the container is substantially unexposed to the surrounding atmosphere throughout its production process, whereby the chance of entry of foreign substances into the container can be reduced significantly.

A description will next be made of a second embodiment of the present invention. In the second embodiment, the side channel is in a tubular form.

FIG. 15 is a schematic plan view of a filled and sealed, self-contained mixing container according to the second embodiment of the present invention, in which two types of contents are stored. FIG. 16 is a cross-sectional view of the container taken along line XVI—XVI of FIG. 15.

In the filled and sealed container according to the second embodiment, which is generally designated at numeral 101, a first compartment 102 and a second compartment 103 which have been formed by sealing a pair of flexible sheets, said sheets being superimposed in a face-to-face relation, along peripheral edges thereof are integrally connected to each other with an isolation zone 107 interposed therebetween. The first compartment 102 and the second compartments 103 are connected together such that they can be communicated to each other via a side channel 106 bonded to outer surfaces 105,105 of walls 104,104 of the respective compartments 102,103.

The side channel 106 is composed of a flow passage 108 and an isolator 109. The flow passage 108 has been constructed to permit movement of the contents stored in one of the compartments to the other compartment, while the isolator 109 has been formed to store the contents of the respective compartments in an manner isolated from each other until use, in other words, until they are mixed together. By destroying the isolator 109 at the time of mixing, the flow passage 108 can be completed to achieve communication between the compartments.

No particular limitation is imposed on the structure of the side channel 106 as long as the flow passage 108 can be completed by the destruction of the isolator 109 at the time of mixing.

The side channel in the second embodiment is tubular. Different from the bubble-like configuration according to the first embodiment described above, a member which is different from any compartment-defining walls is employed as the isolator.

Figure 17:
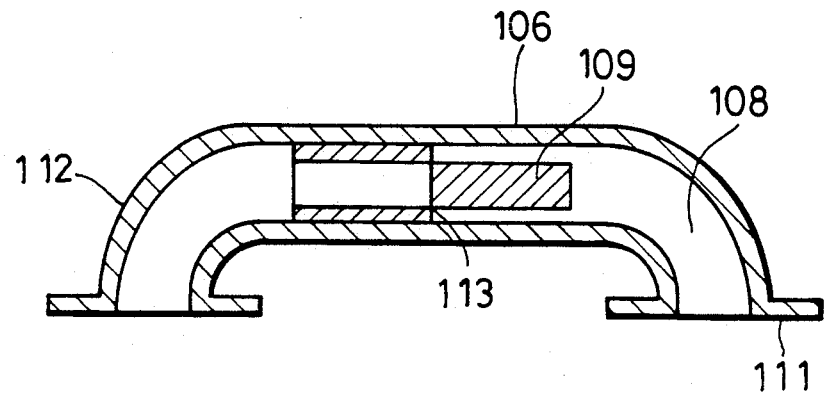
FIG. 17 is a schematic cross-sectional view showsecond example of the tube-type side channel.

FIG. 17 is a cross-sectional view showing one example of the structure of the side channel 106. The side channel 106 is constructed of flange portions 111, a tube portion 112 and the isolator 109. The flange portions 111 has been adapted to bond the side channel 106 to the walls 104 of the container 101. The tube portion 112 has flexibility and defines the flow passage 108 which is adapted to communicate the compartments 102,103 to each other. The isolator 109 is provided inside the flow passage 108 at a longitudinal midpoint of the flow passage 108 to keep the flow passage 108 closed until use so that forward and rearward sections of the flow passage 108 can be maintained isolated from each other. At the time of use, the isolator 109 is broken off at an opening point 113 so that the flow passage 108 can be completed.

When the container 101 of the second embodiment is used for a therapeutic purpose, it is desirable, as structural features to be used upon administration of medical fluids to the body subsequent to their mixing in the container 101, to provide the container 101 with an outlet member 120, namely, a port for permitting discharge of the medical fluids from the container—at one end of the container—and with a suspension hole 130, namely, a hole adapted to hang up the container on a irrigator stand—at the other end of the container. The present invention permits provision of outlet members and suspension holes as many as desired and also allows to choose their dimensions and locations as needed, both in view of convenience in use. Incidentally, an opening of the outlet member 120 is generally closed by a cap assembly which is composed of a rubber plug 121, a cap 122 and a diaphragm 123 preventing direct contact of the medical fluid with the rubber plug 121. This is however not an essential requirement.

At the time of use, the flow passage 108 can be easily completed by simply bending the flexible tube portion from the outside and breaking off the isolator 109 at the opening point 113. The first compartment 102 and the second compartment 103 are hence communicated with each other so that the two types of medical fluids sealed in the respective compartments can be mixed easily without their exposure to the external atmosphere.

The side channel 106 is constructed independently from the container itself. Since the side channel 106 is bonded to the outer surfaces 105,105 with the flanges 111 being maintained in close contact with the outer surfaces 105,105, a very simple method can be chosen for the bonding between the side channel 106 and the walls 104 of the container 101. As a result, the production process and facilities can be very simplified, leading to improved production stability and hence to an economical production cost. In addition, the container can be produced under such conditions that the inside of the container is substantially unexposed to the surrounding atmosphere throughout its production process, whereby the chance of entry of foreign substances into the container can be reduced significantly.

The isolator 109 can be destroyed easily in the second embodiment since the first and second compartments 102,103 are formed independently from the side channel 106, on other words, the isolator 109 can be formed long by making the side channel 106 longer without increasing the overall length of the container 101.

Further, the tube portion 112 can be covered by a rigid case or the like to avoid any accidental breakage of the isolator 109 during transportation or the like.

Figure 18:
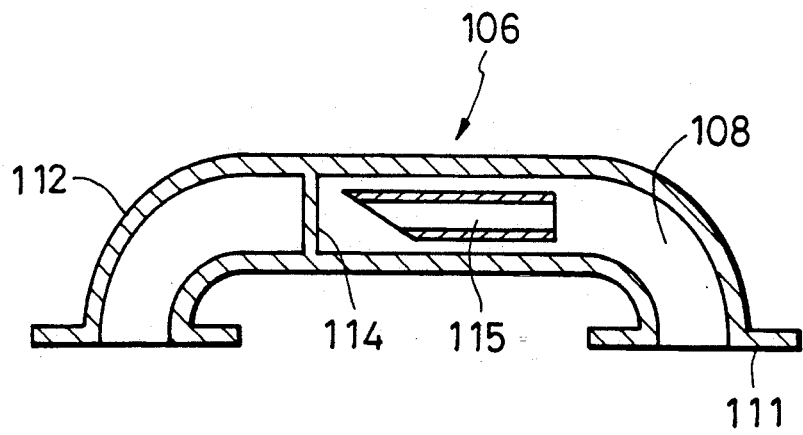
FIG. 18 is a schematic cross-sectional view showing a second example of the tube-type side channel.

In the case of the side channel 106 shown in FIG. 17, the means for destroying the isolator 109 is built in the isolator 109 itself. The present invention however allows to employ a structure such that, as illustrated in FIG. 18, a film-like isolator 114 is provided and a pointed, molded member 115 is additionally provided as a destroying member for the isolator 114 in the side channel 106. Since the tube portion 112 is flexible, the isolator 114 can be easily destroyed to form an opening therethrough in a similar manner to the structure of FIG. 17.

A description will next be made of a process for the production of a container according to the present invention.

Firstly, a container portion is obtained by forming its walls with two plastic sheets which are superimposed.

The plastics employed for the walls of the container can be selected from conventional thermoplastic resins having flexibility, for example, from soft polyesters, chlorinated polyethylene resins, vinyl chloride resin, ethylene-vinyl acetate-vinyl chloride graft polymers, ethylene-vinyl acetate copolymers, low-density polyethylene resin, linear low-density polyethylene resin, polybutadiene resin, polybutene resin and polypropylene resin and copolymers and blends of these resins. The production process imposes practically no limitation to the type of the plastics. Since a side channel is bonded to a two-dimensionally spreadable outer surface of one of the walls of the container, heat sealing or a bonding method making use of an adhesive can be employed in addition of high-frequency welding. In view of this, there is substantially no limitation to the type of plastics usable to form the walls of the container. Even a resin having a small dielectric loss, for example, a polyolefin resin can therefore be employed without problems.

Polyolefin resins are particularly preferred when the container is used as a container to be filled with medical fluids for therapeutic application because they have an especially high level of safety and they are available at a low price.

The plastic can therefore be selected from ethylene-vinyl acetate copolymers, low-density polyethylene resin, linear low-density polyethylene resin, polybutadiene resin, polybutene resin and polypropylene resin and copolymers and blends of these resins.

In addition, use of a multilayer plastic sheet having two or more layers as a plastic sheet can facilitate the setting of heating conditions for welding the side channel with the plastic sheet. Resins having different welding temperatures can be used as a resin forming the innermost layer of the sheet, said innermost layer forming the inner surface of the container portion, and as a resin forming the outermost layer of the sheet, said outermost layer serving as the outer surface of the container portion, respectively. By choosing the resin forming the innermost layer and that forming the outermost layer in such a way that the former has a higher welding temperature than the latter, it is possible to facilitate the setting of the heating conditions under which the inner surfaces of the plastic sheets are not welded to each other but the side channel and the outer surface of one of the plastic sheet can be welded.

If polyolefin resins are used in both outermost and innermost layers, suited for use as materials for the filled and sealed container of this invention are, for example, sheets of such a construction that the resin forming the outermost layer is a polyolefin resin, preferably, a linear low-density polyethylene resin and the resin forming the innermost layer is a resin blend of the resin for forming the outermost layer and another polyolefin resin having a heat-sealing starting temperature higher than the former resin, preferably, a resin blend of the linear low-density polyethylene resin and a polypropylene resin.

When a resin blend is used to form the innermost layer, the suitable proportions of its blending resins varies depending on the mutual miscibility of the blending resins, such as the kinds of the blending resins employed and the degrees of their copolymerization, and the sealing temperature. Preferably, the proportion of the resin or resins having a higher welding temperature (heat-sealing starting temperature) than that of any of the resins forming the outermost layer can be in a range of 10-90 wt. % of said resin blend forming the innermost layer. More preferably, the resin or resins having the higher welding temperature can be a propylene homopolymer or copolymer and can amount to 20-80 wt. %. To make the production conditions, i.e., the bonding conditions more stable, the highest heat-sealing starting temperature of the resins forming the innermost layer is higher by 8° C. or more compared to that of the resins forming the outermost layer.

The heat-sealing starting temperature of the resin forming the innermost layer of each wall can be made higher than that of the resin forming the outermost layer of the wall without using such a resin blend. This can be achieved by the combination of high-density polyethylene for the innermost layer and low-density polyethylene or linear low-density polyethylene for the outermost layer or by the combination of polypropylene for the innermost layer and low-density polyethylene or linear low-density polyethylene for the outermost layer.

The plastic sheets serving as the walls of the container may be either single-layer or multi-layer plastic layers, which can be formed by any suitable forming or molding method such as inflation molding, blow molding, extrusion or calendering. One of the advantages of the filled and sealed container of the present invention, namely, little inclusion of foreign substances cannot however be expected unless the adhesion of foreign substances to at least the surfaces adapted to form the inner surfaces of the container can be maintained little during the formation of the plastic sheets. Of the molding and forming methods referred to above, inflation molding or blow molding is therefore preferred as it permits formation of the sheets without exposure of their inner surfaces to an external atmosphere in which foreign substances are suspended. This however does not mean that other molding or forming methods are unusable, because they can also produce, depending on the manner of control during or after the molding or forming, plastic sheets with little adhesion of foreign substances on the sides to be used as the inner surfaces of the container.

On the other hand, as the resin for forming the side channel, a resin having sufficient miscibility with the resin employed to form the outermost layer can be selected from the above-described resins. It is preferable to choose the same resin as that employed for the outermost layer or its injection molding grade. The resin for the base of the bubble-type side channel can be chosen similarly.

As a resin for the formation of the isolator in each tube-type side channel, it is necessary to choose a resin suited for the structure of the isolator. Where the isolator has a shape such as that illustrated in FIG. 17, the resin can be chosen from relatively hard resins such as polypropylene resin, high-density polyethylene resin, polycarbonate resins, vinyl chloride resins and polyester resins. Heat sealing is preferred as a method for sealing the isolator inside the side channel. Bonding with an adhesive, close contact by blocking, sealing by fitting, or the like can however be chosen.

The outlet member can be molded by injection molding from a resin such as low-density polyethylene resin, high-density polyethylene resin, linear low-density polyethylene resin or polypropylene resin. The outlet member can then be fixed to the container portion by welding or the like.

Incidentally, the term "heat sealing starting temperature" as used herein indicates the lowest temperature at which items to be welded are melted and substantially bonded together when they are heated for a predetermined constant time (for example, this time was set at 20 seconds herein) while being kept in close contact to each other.

As a heating means, it is possible to use an impulse heater or a means making use of heat produced by ultrasonic waves, high-frequency electric fields, high-frequency induction or the like, to say nothing of a conventional heater.

A description will next be made of a method for the production of the first embodiment in which the bubble-type side channel is used as shown in FIG. 1. The description will be made using sheets prepared by calendering or T-die extrusion. First of all, the sheets are cut in predetermined dimensions. Next, by welding, the peripheral seal 11 and the isolation zone 7 are formed to construct the container portion 3 (spaces for the insertion of nozzles should be retained to the injection of the contents). After the welding, unnecessary parts outside the suspension hole 9 and the outer peripheral seal 11 are cut off. Next, the communication enclosure 21 and base 24 are welded such that the two plastic sheets adapted to construct the container portion 3 be sandwiched between the enclosure 21 and the base 24. Here, it is important to set the heating conditions such that the plastic sheets themselves are not welded but the communication enclosure 21 and the plastic sheet as well as the base 24 and the plastic sheet ca be welded.

The heating conditions for the welding between the communication enclosure 21 and the plastic sheet and between the base 24 and the plastic sheet are basically determined by setting the heating temperature, heating time and pressing pressure. Selection of a suitable heating method further facilitates the setting of the heating conditions. When heating by the welding dies 51,52 shown in FIG. 11, welding between the plastic sheets themselves can be minimized provided that the plastic sheets are alternately welded with the communication enclosure 21 and the base 24, respectively by alternately heating the welding dies 51,52.

To have the side channel bonded to the outer surface of the corresponding wall of the container while maintaining the former in close contact with the latter, the outer surface of the wall of the container, said outer surface being bonded with the side channel, is required to be substantially a flat surface or to be a surface spreadable as a flat surface.

On the other hand, in the second embodiment in which the tubular side channel is used (see FIG. 15), the side channel is bonded to one of the walls of the container. It is therefore necessary that through-holes are formed through the wall at the positions corresponding to the side channel but no through-holes are formed through the other wall of the container at positions opposing the first-mentioned through-holes. In this case, by forming holes through the superimposed walls of the container without separation of the walls, closing the holes in one of the walls, bringing the flange portions of the side channel into close contact with the outer surface of the hole-defining walls with the flow passage being in registration with the flange portions, pressing a heating means against the outer surface of the other wall, said wall being different from that being kept in close contact with the flange portions, without opening the superimposed walls of the container, and then completing the welding of the flange portions with the closely-contacted surface of the associated wall before the walls of the container are welded together, the container can be produced under conditions such that the interior of the container is substantially unexposed to the surrounding atmosphere throughout the production process. Where it is difficult to choose conditions under which the flange portions can be welded to the outer surface of the associated wall without mutual welding of the superimposed walls of the container, more reliable and stable bonding can be achieved by using multilayer sheets in which the resin forming the layers facing the inside of the container is higher in heat sealing starting temperature than the resin forming the layers facing the outside of the container.

A description will next be made of contents to be stored in the container. Plural kinds of contents are used, which contain components susceptible to mutual reaction.

The term "susceptible to mutual reaction" as used herein means primarily that a chemical substance tends to undergo a chemical reaction when brought into contact with another chemical substance. Examples of the reaction include all liquid-liquid phase reactions, vapor-vapor phase reactions, solid-solid phase reactions, liquid-vapor phase reactions, liquid-solid phase reactions and vapor-solid phase reactions. In the case of a solid phase-solid phase reaction, each of plural contents forming the solid phases is preferably either in a powdery form or in a granular form which has flowability. In other words, the present invention is useful basically to prevent plural flowable contents from undergoing a mutual reaction during transportation or storage. It is, however, not necessary that each of the plural contents has flowability. The present invention can be practiced insofar as at least one of the plural contents is a flowable substance, because the flowable contents can flow through the side channel and can then contact the other contents. The proportions in amount of the individual contents ca be determined pursuant to the application purpose. No limitation is imposed in this respect from the shape or structure of the container.

No particular limitation is imposed on the reaction velocity between the individual contents, in other words, between the components contained in the individual contents. The need for isolation of one component from the other component increases as their reaction velocity becomes higher. Where the contents are intended for storage over a long period of time, it is of course desirable to isolate the individual contents from each other even if the reaction velocity therebetween is low. In the case of a system such that the reaction velocity between its components is accelerated under high-temperature conditions, it is indispensable to isolate the individual contents from each other.

Reactable combinations of substances include, for example, glucose and amino acids; aqueous media and various vitamins; starch/proteins and various enzymes; metal ions and chelating agents; unsaturated fatty acids, metal ions and enzymes; acids and alkalis; aqueous media and salts; and aqueous media and antibiotics; aqueous media and carcinostatic substance. Exemplary reactions include Maillard reactions, hydrolyses, oxidations, reductions, various enzyme reactions, and the like.

The container according to the present invention makes it possible to perform full mixing of its plural contents within the container. In addition, the container can be formed without substantial exposure of its inside to the external atmosphere through its production process. containers according to the present invention can therefore be suitably employed in fields where a closed system is required. From this viewpoint, specific exemplary combinations of contents include IVH base solutions or hypertonic glucose solutions and amino acid solutions in IVH useful in closed therapeutic systems; powder medicines and liquid medicines in elemental diet, and the like. The components of these contents are generally prone to quality modifications or coloration when subjected to thermal sterilization as single-pack preparations. They also tend to undergo quality modifications during storage. Unless their mixing is performed under closed conditions, problems such as dispensing error and contamination tend to occur.

When employed as bags for medical fluids, the filled and sealed containers according to the present invention can prevent quality modifications of their contents during autoclave sterilization treatment or storage and are also expected to avoid contamination with bacteria upon mixing the medical fluids in a hospital.

EXAMPLES

The present invention will hereinafter be described more specifically by the following examples.

EXAMPLE 1

Using linear low-density polyethylene (density: 0.922 g/cm$^3$), an inflation tube having a flat width of 250 mm and a thickness of 0.25 mm was formed by inflation molding. The inflation tube was heat sealed at 160° C. for 5 seconds so that an outer peripheral seal and an isolation zone were formed as shown in FIG. 1. It is to be noted that the outer peripheral seal was not sealed at some locations to leave nozzle-receiving openings for the injection of two types of contents. An outer peripheral edge portion of the outer peripheral seal and the portion corresponding to a suspension hole were punched off. On the side, a molded article as the outlet member shown in FIG. 1 was produced by injection molding from linear low-density polyethylene (density: 0.920 g/cm$^3$). The outlet member was then bonded to the inflation tube which had been sealed along the outer periphery thereof.

Figure 11:
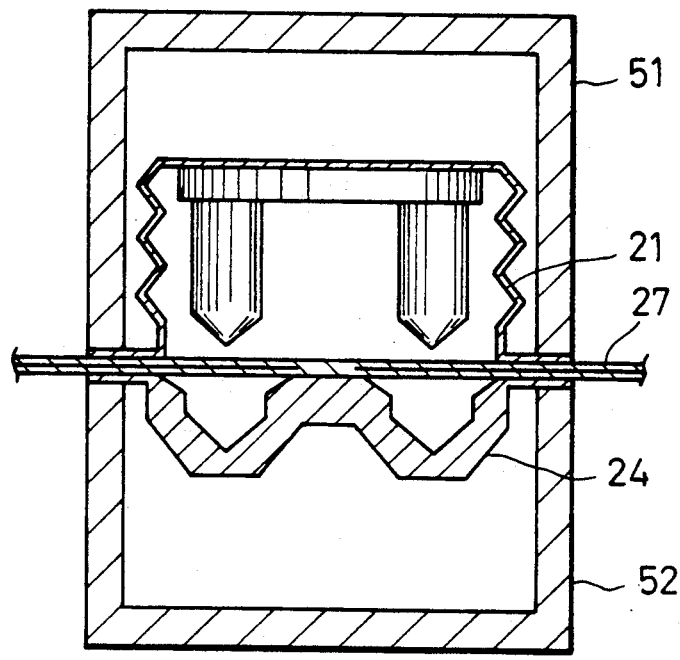
FIG. 11 is a schematic cross-sectional view showing thermal welding of the side channel to a container portion.

Next, using linear low-density polyethylene (density: 0.935 g/cm$^3$), the communication enclosure and base depicted in FIG. 2 were formed by injection molding. Further, from polypropylene with a glass filler incorporated therein, the puncture means shown in FIG. 2 were produced by injection molding. The puncture means was fixed on the communication enclosure by welding. The resultant sub-assembly and the base were then arranged by welding dies for 5 seconds, respectively as illustrated in FIG. 11. The lower welding die was cooled to room temperature and the upper welding die was then heated at 200° C., whereby the communication enclosure was bonded to an outer surface of one side of the inflation tube. At that time, the both sides of the inflation tube was not bonded together.

A medical fluid container was produced as described above.

A base solution (600 ml) for IVH was charged into a first compartment of the container. An opening of the outlet member was sealed by a film made of linear low-density polyethylene. A rubber plug was then fitted in the opening of the outlet member. On the other hand, an amino acid solution (300 ml) was charged into a second compartment through a nozzle which had been inserted in an opening left in the outer peripheral seal. The opening was then heat-sealed.

The medical fluid container was subjected to autoclaved sterilization at 115° C. for 40 minutes. After the sterilization, neither any substantial deformation nor any communication between the first and second compartments was however observed. In addition, a leakage test was conducted under elevated pressure. Leakage of the liquid contents was not observed at any one of the heat-sealed or welded parts.

Next, the communication enclosure of the side channel was pressed to make the puncture members penetrate through the inflation tube. As a result, the amino acid solution in the second compartment was introduced into the first compartment by way of through-holes thus formed, whereby the amino acid solution and the base solution for IVH were mixed in the first compartment.

Pursuant to conventional transfusion procedures, a spike needle of a transfusion set was caused to penetrate through the opening of the outlet member. The height of the medical fluid container was adjusted such that the height from a phlebotomy needle to the opening of the outlet member became 70 cm. Further, the dropping rate was controlled at about 50 ml per minute by a clamp. Measurement of the relationship between the flow rate and time indicated that the flow rate was substantially proportional to time.

EXAMPLE 2

Using linear low-density polyethylene (density: 0.922 g/cm$^3$) for an outer layer and a 1:1 resin blend of linear low-density polyethylene (density: 0.90 g/cm$^3$) and polypropylene (density: 0.90 g/cm$^3$) for an inner layer, a two-layer inflation tube having a flat width of 250 mm and a thickness of 0.25 mm was formed by inflation molding. The inflation tube was heated at 230° C. for 5 seconds except at some positions to be employed as openings for contents-injecting nozzles, so that an outer peripheral seal and an isolation zone were formed as shown in FIG. 1. An outer peripheral edge portion of the outer peripheral seal and the portion corresponding to a suspension hole were punched off. On the side, a molded article as the outlet member shown in FIG. 1 was produced by injection molding from linear low-density polyethylene (density: 0.920 g/cm$^3$). The outlet member was then bonded to the inflation tube which had been sealed along the outer periphery thereof.

Next, using linear low-density polyethylene (density: 0.935 g/cm$^3$), the communication enclosure and base depicted in FIG. 2 were formed by injection molding. Further, from polypropylene with a glass filler incorporated therein, the puncture means shown in FIG. 2 were produced by injection molding. The puncture means was fixed on the communication enclosure by welding. The resultant sub-assembly and the base were then arranged by welding dies, respectively as illustrated in FIG. 11. The resulting assembly was heated at 190° C. for 4 seconds from both upper and lower sides, whereby were bonded the communication enclosure and the upper side of the inflation tube as well as the base and the lower side of the inflation tube. At that time, the upper and lower sides of the inflation tube was not bonded together.

A medical fluid container was produced as described above.

A base solution (600 ml) for IVH was charged into a first compartment of the container. An opening of the outlet member was sealed by a film made of linear low-density polyethylene A rubber plug was then fitted in the opening of the outlet member. On the other hand, an amino acid solution (300 ml) was charged into a second compartment through a nozzle which had been inserted in an opening left in the outer peripheral seal. The opening was then heat-sealed.

The transfusion container was subjected to autoclaved sterilization at 115° C. for 40 minutes. After the sterilization, neither any substantial deformation nor any communication between the first and second compartments was however observed. In addition, a leakage test was conducted under elevated pressure. Leakage of the liquid contents was not observed at any one of the heat-sealed or welded parts.

Next, the communication enclosure of the side channel was pressed to make the puncture members penetrate through the inflation tube. As a result, the amino acid solution in the second compartment was introduced into the first compartment by way of through-holes thus formed, whereby the amino acid solution and the base solution for IVH were mixed in the first compartment.

Pursuant to conventional transfusion procedures, a spike needle of a transfusion set was caused to penetrate through the opening of the outlet member. The height of the medical fluid container was adjusted such that the height from a phlebotomy needle to the opening of the outlet member became 70 cm. Further, the dropping rate was controlled at about 50 ml per minute by a clamp. Measurement of the relationship between the flow rate and time indicated that the flow rate was substantially proportional to time.

EXAMPLE 3

Formed by a multilayer inflation molding machine was a multilayer inflation sheet having a flat width of 250 mm. The multilayer inflation sheet had as an inner layer a 30-$\mu$m thick layer (heat-sealing starting temperature: 156° C.) formed of a 1:1 resin blend of linear low-density polyethylene ("NIPOLON-L", trade name; product of TOSOH Corp.; density: 0.925 g/cm$^3$; MI: 0.8) and polypropylene ("CHISSO POLYPRO", trade mark; product of Chisso Corporation; density: 0.90 g/cm$^3$; MI: 0.7); and as an outer layer a 220-$\mu$m thick layer (heat-sealing starting temperature 117° C.) formed of linear low density polyethylene ("NIPOLON-L", trade name; product of TOSOH Corp.; density: 0.925 g/cm$^3$; MI: 0.8).

On the side, from linear polyethylene ("NIPOLON-L", trade name; product of TOSOH Corp.; density: 0.920 g/cm$^3$; MI: 20), a cylindrical molded article having an internal diameter of 6.6 mm and an external diameter of 8 mm was produced as a tube-type side channel, with flanges formed at opposite ends of the cylindrical molded article. The flanges had a thickness of 0.7 mm and an outer diameter of 14 mm. In addition, from the same linear polyethylene, another cylindrical molded article having an inner diameter of 17 mm and an outer diameter of 21 mm was produced as an outlet member, with a flange formed at one end of the cylindrical molded article. The flange had a thickness of 1 mm and an outer diameter of 37 mm.

Molded next with a polycarbonate resin ("NOVAREX", trade mark; product of Mitsubishi Kasei Corporation) was the isolator shown in FIG. 17 (side channel 106, isolator 109, flow passage 108, flange 111, tube 112, opening point 113), namely, the isolator consisting of a cylindrical portion having an inner diameter of 4 mm, an outer diameter of 7 mm and a length of 15 mm and a rod-like portion having an outer diameter of 5 mm and a length of 12 mm, closing one of open ends of the cylindrical portion and connected to the open end of the cylindrical portion by way of a thin wall portion. The flow passage of the side channel was blocked by pushing the isolator into the side channel (If a side channel is elastic enough, an adhesive or a welding process is not always necessary.).

The inflation sheet was then cut with a width of 200 mm. The outlet member was bonded to one of the two sides of the inflation tube and a suspending portion defining a suspension hole was formed on the other side. Both the sides were heat-sealed along their outer peripheries so that a container was produced. To divide the container into two compartments, one on a side of the suspension hole and the other on a side of the outlet member, the container was heat-sealed near the center thereof so that an isolation region was formed.

Next, at a position on one of the walls of the compartment on the side of the suspension hole and also at a position on one of the walls of the compartment on the side of the outlet member, at which positions the side channel were to be bonded to the associated walls of the compartments, holes were formed by a punch in such a way that the holes penetrated through both the walls of the respective compartments, namely, the superimposed, upper and lower sheets. The side channel with its flow passage blocked by the isolator was then brought into close contact with the outer surface of one of the punched walls of one of the two compartments and also with the outer surface of one of the punched walls of the other compartment, the former one wall and the latter one wall being on the same side of the container, such that the flange portions of the side channel were registered with the corresponding holes. Without separation of the superimposed walls of the container, a hot plate which had been heated to 145° C. was then maintained in substantially pressure-free contact with the outer surfaces of the other walls of the compartments, said the other walls being the ones other than the walls with which the flange portions were being kept in close contact, for 15 seconds via a TEFLON (trade mark)-coated glass fiber cloth, whereby the side channel was bonded to the associated walls of the compartments. The holes formed in the opposite side of the container were closed by heat-sealing a sheet of the same material as the side channel thereto in a similar manner. As a result, there was obtained a container in which the side channel is firmly bonded with its the associated walls of the compartments but the walls on one side of the container were not heat-sealed with the walls on the other side the container.

Incidentally, the outer peripheral seal between the walls on both the sides of the container was formed by heating the corresponding portions with an impulse heat sealer ("FA-30-5w Model", trade name; manufactured by Fuji Impulse Co., Ltd.) under heat-sealing conditions which consisted heating for 1.5 seconds and subsequent cooling for 5 seconds. Further, the sealing of the suspending portion was effected by a heat sealer manufactured by the assignee company (Material Engineering Technology Laboratory Inc.) via a 0.1-mm thick TEFLON-coated glass fiber cloth under heat-sealing conditions which consisted of heating at 170° C. for 12 seconds.

Through the outlet member and the filling opening formed in outer peripheral seal of the container, the respective compartments were next charged with 300 ml and 150 ml of distilled water filtered through a membrane filter having a pore size of 0.45 µm, namely, the purified water for fine particle test as prescribed in The Pharmacopoeia of Japan. After the outlet member and filling opening were sealed, the container was subjected to autoclave sterilization treatment. Subsequent to confirmation of the container being free from leakage, the isolator assembled in the side channel was broken off to communicate the compartments to each other. As a result, the water filled in the compartment on the side of the suspending portion was successfully moved with ease into the compartment on the side of the outlet member. Further, the level of contamination of the filled water by foreign substances was investigated following the testing method for fine, insoluble particles in injections, which is prescribed in The Pharmacopoeia of Japan. The contamination level was found to meet the standard.

EXAMPLE 4

The other side channel which is illustrated in cross-section in FIG. 18 (side channel 106, flange 111, isolator 114, pointed, molded article 115, flow passage 108, tube 112) was formed in the following manner. Namely, a cylindrical, molded article having an inner diameter of 6.6 mm and an outer diameter of 8 mm was formed from linear polyethylene ("NIPOLON-L", trade name; product of TOSOH Corp.; density: 0.920 g/cm$^3$; MI: 20), with flanges of 0.7 mm thickness and 8 mm outer diameter being provided on opposite ends of the cylindrical, molded article and an isolator wall of 0.2 mm thickness being formed as an insulator at an intermediate point. In addition, a pointed, molded article having an inner diameter of 3 mm, an outer diameter of 5 mm and a length of 15 mm was also formed from polypropylene ("CHISSO POLYPRO", trade mark; product of Chisso Corporation; density: 0.90 g/cm$^3$; MI: 0.7). The latter molded article was enclosed on one side of the isolation wall of the former molded article, with the pointed end facing toward the isolator wall.

In a similar manner to Example 3, a container was next produced, the purified water for fine particle test was filled in the respective compartments through an outlet member and a filling opening, respectively, the outlet member and filling opening were sealed, and the container was then subjected to autoclave sterilization treatment. Subsequent to confirmation of the container being free from leakage, the pointed, molded article was caused to penetrate through the isolator wall built in the side channel to communicate the compartments to each other. As a result, the water filled in the compartment on the side of the suspending portion was successfully moved with ease into the compartment on the side of the outlet member. Further, the level of contamination of the filled water by foreign substances was investigated in a similar manner to Example 3. The contamination level was found to meet the standard.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A flexible, plastic, filled and sealed, self-contained mixing container consisting of plural compartments with contents enclosed therein in a manner mutually isolated from each other, said container comprising:
   at least one heat-sealed to a single-plane outer surface of the wall of the container, said at least one side-channel, which is contiguous to at least two compartments, contains a means to destroy a portion of the wall of the container at at least one location, in order to mix the contents together, and is hollow over the portion of the wall to be destroyed.

2. The container of claim 1, wherein the at least one side-channel is formed in a bubble-shape.

3. The container of claim 1, further comprising a base provided on one side of the container, said one side being opposite to the surface on which the at least one side-channel is formed, the base cooperating with the destroying means so that a portion of the wall the base covers is also destroyed at at least one location, and the base itself forms a second side-channel in which to mix the contents of the plural compartments.

4. The container of claim 1, wherein the wall of the container is made of a multilayer sheet, the heat-sealing starting temperature of a resin forming the layer facing the inside of the container is higher than that of another resin forming the layer facing the outside of the container, and the layer facing the outside and the at least one side-channel are heat-sealed to each other.

5. The container of claim 4, wherein the multilayer sheet is formed of polyolefin resins, and the resin forming the layer facing the inside is a resin blend of at least two polyolefin resins.

6. The container of claim 5, wherein 10–90 wt. % of said resin blend of at least two polyolefin resins consists of the resin or resins among said blend having a higher heat-sealing starting temperature than that of any of the resins forming the layer, facing the outside.

7. The container of claim 6, wherein there is a difference of at least 8° C. between the highest heat-sealing temperatures of the resins forming the layers facing the inside and the outside of the multilayer sheet.

8. The container of claim 5, wherein the resin blend comprises 80–20 wt. % of a linear, low-density polyethylene resin and 20–80 wt. % of a polypropylene resin.

9. The container of claim 4, wherein the multilayer sheet is formed of two layers, the layer facing the outside being formed of a linear, low-density polyethylene resin, and the layer facing the inside being formed of a resin blend comprising a linear, low-density polyethylene resin and a polypropylene resin.

10. The container of claim 1, wherein the wall of the container has been formed by inflation molding or blow molding.

11. The container of claim 1, wherein at least one of the plural compartments has an outlet member for discharging the contents of the compartments, at least one of the plural compartments has a suspension portion for hanging the container, and the contents are therapeutic preparations.

12. The container of claim 11, wherein the preparations are a base solution for IVH or hypertonic glucose solution and an amino acid solution.

13. The container of claim 12, wherein the preparations are a powdered drug preparation and a liquid drug preparation for elemental diet.

* * * * *